United States Patent
Lindemann et al.

(10) Patent No.: US 11,858,837 B2
(45) Date of Patent: Jan. 2, 2024

(54) VARYING WATER LEVEL SOLIDS AND TRACKING CONTROL

(71) Applicant: Evoqua Water Technologies LLC, Pittsburgh, PA (US)

(72) Inventors: Timothy Lee Lindemann, Jefferson, WI (US); Michael Casey Whittier, Veron, WI (US)

(73) Assignee: Evoqua Water Technologies LLC, Pittsburgh, PA (US)

( * ) Notice: Subject to any disclaimer, the term of this patent is extended or adjusted under 35 U.S.C. 154(b) by 149 days.

(21) Appl. No.: 17/099,112

(22) Filed: Nov. 16, 2020

(65) Prior Publication Data

US 2021/0309548 A1 Oct. 7, 2021

Related U.S. Application Data

(62) Division of application No. 15/760,006, filed as application No. PCT/US2016/049809 on Sep. 1, 2016, now Pat. No. 10,843,948.

(60) Provisional application No. 62/219,735, filed on Sep. 17, 2015.

(51) Int. Cl.
- *C02F 3/00* (2023.01)
- *C02F 3/12* (2023.01)
- *G16H 10/40* (2018.01)

(52) U.S. Cl.
CPC ............ *C02F 3/006* (2013.01); *C02F 3/1263* (2013.01); *G16H 10/40* (2018.01); *C02F 2209/10* (2013.01); *C02F 2209/42* (2013.01); *Y02W 10/10* (2015.05); *Y02W 10/37* (2015.05)

(58) Field of Classification Search
CPC .... C02F 3/006; C02F 3/1263; C02F 2209/10; C02F 2209/42; C02F 11/00; C02F 2209/44; C02F 2209/40; G16H 10/40; Y02W 10/10; Y02W 10/37; B01D 21/34;
(Continued)

(56) References Cited

U.S. PATENT DOCUMENTS

| | | |
|---|---|---|
| 3,923,655 A | 12/1975 | McKinney |
| 5,205,936 A | 4/1993 | Topnik |
| 5,421,995 A | 6/1995 | Norcross |

(Continued)

FOREIGN PATENT DOCUMENTS

| | | | |
|---|---|---|---|
| JP | 2001183354 | * | 7/2001 |
| JP | 2002340656 | * | 11/2002 |

OTHER PUBLICATIONS

English language machine translation of JP2001-183354, 5 pages, No Date.*

(Continued)

*Primary Examiner* — Pranav N Patel

(57) ABSTRACT

A sequencing batch reactor includes a liquid level sensor configured to measure a level of liquid in the vessel and provide an indication of the level of the liquid to a controller and a sludge detector configured to measure a position of an interface between sludge and solids-lean supernatant in the vessel and to provide an indication of the position of the interface to the controller. The controller is configured to perform a comparison between the level of the liquid and the position of the interface and control an amount of solids-lean supernatant removed from the vessel during the decant stage based on the comparison.

15 Claims, 11 Drawing Sheets

(58) Field of Classification Search
CPC .... B01D 21/2444; B01D 21/30; B01D 21/32; B01D 21/245; B01D 21/307
See application file for complete search history.

(56) References Cited

U.S. PATENT DOCUMENTS

| | | |
|---|---|---|
| 6,216,540 B1 | 4/2001 | Nelson et al. |
| 2009/0283457 A1 | 11/2009 | Buchanan et al. |
| 2015/0032411 A1* | 1/2015 | Hoferer ................. G01F 23/284 |
| | | 702/154 |

OTHER PUBLICATIONS

English language machine translation of JP2002-340656, 6 pages, No Date.*
El-Ghafari, Rasha, "Requisition by the Examiner in Accordance With Subsection 86(2) of the Patent Rules", issued for related Canadian patent application No. 2,996,068, dated Jun. 10, 2022, 4 pages.
Young, Lee W., "Written Opinion of the International Searching Authority", International Application No. PCT/US2016/049809, dated Jun. 21, 2017, 8 pages.
Young, Lee W., "International Search Report", International Application No. PCT/US2016/049809, dated Jun. 21, 2017, 2 pages.
Bai, Lingfei, "International Preliminary Report on Patentability", International Application No. PCT/US2016/049809, dated Mar. 20, 2018, 9 pages.
Dias-Abey, Asoka, "Examination report No. 1 for standard patent application", Australian Patent Application No. 2016322487, dated Jun. 29, 2021, 3 pages.
El-Ghafari, Rasha, "Examination Report", Canadian patent application No. 2,996,068, dated Jan. 25, 2023, 4 pages.

* cited by examiner

VARYING WATER LEVEL SOLIDS AND TRACKING CONTROL

CROSS-REFERENCE TO RELATED APPLICATION

This application claims priority under 35 U.S.C. § 119(e) to U.S. Provisional Application Ser. No. 62/219,735, titled "VARYING WATER LEVEL SOLIDS AND TRACKING CONTROL," filed on Sep. 17, 2015 which is incorporated herein by reference in its entirety for all purposes.

BACKGROUND

Aspects and embodiments disclosed herein are generally directed to the structure and operation of sequencing batch reactors (SBRs) and to control systems for same.

SUMMARY

In accordance with an aspect of the present invention, there is provided a wastewater treatment system. The system comprises a sequencing batch reactor vessel configured to perform biological treatment of wastewater in a series of treatment stages including a fill stage, a biological reaction stage, a sludge settling stage in which solids settle from the wastewater to form a sludge and a solids-lean supernatant, a solids-lean supernatant decant stage, and an idle stage. The fill stage includes introducing a non-predetermined amount of wastewater into the vessel. The system further comprises a liquid level sensor configured to measure a level of liquid in the vessel and provide an indication of the level of the liquid to a controller, and a sludge detector configured to measure a position of an interface between the sludge and the solids-lean supernatant in the vessel and to provide an indication of the position of the interface to the controller. The controller is configured to perform a comparison between the level of the liquid and the position of the interface and control an amount of solids-lean supernatant removed from the vessel during the decant stage based on the comparison.

In some embodiments, the sludge detector is further configured to determine a degree of sharpness of the interface and to provide an indication of the degree of sharpness of the interface to the controller.

In some embodiments, the controller is further configured to initiate removal of the solids-lean supernatant responsive to the degree of sharpness of the interface exceeding a predetermined level.

In some embodiments, the controller is further configured to vary a speed of removal of the solids-lean supernatant based at least in part on the degree of sharpness of the interface.

In some embodiments, the controller is further configured to control a rate of sludge removal from the vessel based at least in part on the degree of sharpness of the interface.

In some embodiments, the controller is further configured to decant solids-lean supernatant vessel at a rate that maintains a substantially constant depth of supernatant above the interface.

In some embodiments, the controller is further configured to control an amount of sludge removed from the vessel based at least in part on the position of the interface.

In some embodiments, the sludge detector comprises a plurality of suspended solids sensors each disposed at different fixed locations within the vessel. The plurality of suspended solids sensors may comprise one or more of optical sensors or ultrasonic sensors.

In some embodiments, the sludge detector comprises a sensor that moves vertically responsive to a change in the level of liquid in the vessel. The sludge detector may comprise one of an ultrasonic level sensor or a radar level sensor.

In some embodiments, the liquid level sensor comprises an ultrasonic sensor.

In some embodiments, the liquid level sensor comprises a plurality of sensors each disposed at different fixed levels in the vessel.

In some embodiments, the liquid level sensor and sludge sensor are included in a same sensor.

In some embodiments, the sludge detector comprises an ultrasonic level detector having an operating frequency between about 50 kHz and about 800 kHz.

In some embodiments, the sludge detector comprises a compressed high-intensity radar pulse sonar unit.

In accordance with another aspect, there is provided a method of facilitating control of a wastewater treatment system. The method comprises introducing a volume of wastewater into a sequencing batch reactor vessel of the wastewater treatment system, biologically treating the wastewater in the vessel, maintaining quiescent conditions in the vessel sufficient for solids in the wastewater to settle and form a blanket of settled sludge and a solids-lean supernatant, measuring a level of liquid in the vessel, providing an indication of the level of the liquid to a controller, measuring a position of an interface between the blanket of settled sludge and the solids-lean supernatant in the vessel, providing an indication of the position of the interface to the controller, performing a comparison between the level of the liquid and the position of the interface with the controller, decanting the solids-lean supernatant from the vessel, and controlling an amount of the solids-lean supernatant decanted from the vessel based on the comparison.

In some embodiments, the method further comprises introducing the wastewater into the vessel at a non-predetermined rate.

In some embodiments, the method further comprises determining a degree of sharpness of the interface, and providing an indication of the degree of sharpness of the interface to the controller. The method may further comprise initiating decanting of the solids-lean supernatant responsive to the degree of sharpness of the interface exceeding a predetermined level.

In some embodiments, the method further comprises varying a speed of decanting of the solids-lean supernatant based at least in part on the degree of sharpness of the interface.

In some embodiments, the method further comprises controlling a rate of sludge removal from the vessel based at least in part on the degree of sharpness of the interface.

In some embodiments, the method further comprises controlling an amount of sludge removed from the vessel based at least in part on the position of the interface.

In some embodiments, introducing the volume of wastewater into the vessel includes introducing a non-predetermined volume of wastewater into the vessel.

In some embodiments, the method comprises controlling a rate of decanting of solids-lean supernatant from the sequencing batch reactor vessel to maintain a substantially constant depth of solids-lean supernatant above the interface during settling of the sludge.

In accordance with another aspect, there is provided a method of retrofitting a wastewater treatment system. The method comprises installing a control system in a sequencing batch reactor vessel of the wastewater treatment system. The sequencing batch reactor vessel is configured to perform biological treatment of wastewater in a series of treatment stages including a fill stage, a biological reaction stage, a sludge settling stage in which solids settle from the wastewater to form a blanket of sludge and a solids-lean supernatant, a solids-lean supernatant decant stage, and an idle stage, the fill stage including introducing a non-predetermined amount of wastewater into the vessel. The control system includes a liquid level sensor configured to measure a level of liquid in the vessel and provide an indication of the level of the liquid to a controller, and a sludge detector configured to measure a position of an interface between the blanket of sludge and the solids-lean supernatant in the vessel and to provide an indication of the position of the interface to the controller. The controller is configured to perform a comparison between the level of the liquid and the position of the interface and control an amount of the solids-lean supernatant removed from the vessel during the decant stage based on the comparison.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Figure 1A:
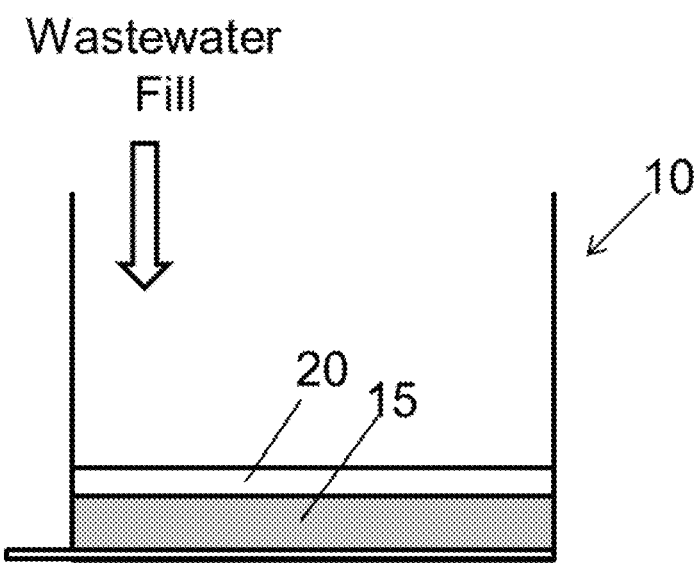
FIG. 1A illustrates a first treatment stage of a sequencing batch reactor.

Aspects and embodiments disclosed herein are not limited to the details of construction and the arrangement of components set forth in the following description or illustrated in the drawings. Aspects and embodiments disclosed herein are capable of being practiced or of being carried out in various ways. Also, the phraseology and terminology used herein is for the purpose of description and should not be regarded as limiting. The use of "including," "comprising," "having," "containing," "involving," and variations thereof herein is meant to encompass the items listed thereafter and equivalents thereof as well as additional items.

Sequencing batch reactors (SBRs) are vessels used in some wastewater treatment systems. SBRs often are utilized for performing the breakdown of solids utilizing an activated sludge process. Wastewater treated in SBRs may include, for example, sewage or output from anaerobic digesters or mechanical biological treatment facilities. Wastewater is typically treated in batches in an SBR. In many implementations, oxygen is bubbled through a mixture of wastewater and activated sludge in an SBR to break down organic matter, often measured as biochemical oxygen demand (BOD) or chemical oxygen demand (COD), to produce a waste sludge and a treated effluent, referred to herein as solids-lean supernatant.

SBRs typically operate in a series of treatment stages including:
A. Fill
B. React
C. Settle
D. Decant
E. Idle In the fill stage (See FIG. 1A), an inlet to an SBR vessel 10 is opened and wastewater is introduced into the SBR vessel 10 and mixed with activated sludge 15 that is either present in the vessel or introduced with the wastewater and possibly with supernatant 20 remaining in the vessel 10 from a previous cycle to form a mixed liquor 25. Mixing of the wastewater, activated sludge 15, and residual supernatant 20 may be performed mechanically under anoxic, anaerobic, or aerobic conditions during and/or after the wastewater is introduced into the SBR vessel 10. In various implementations, the volume and/or rate of introduction of wastewater into the SBR vessel 10 may not be known ahead of time.

Figure 1B:
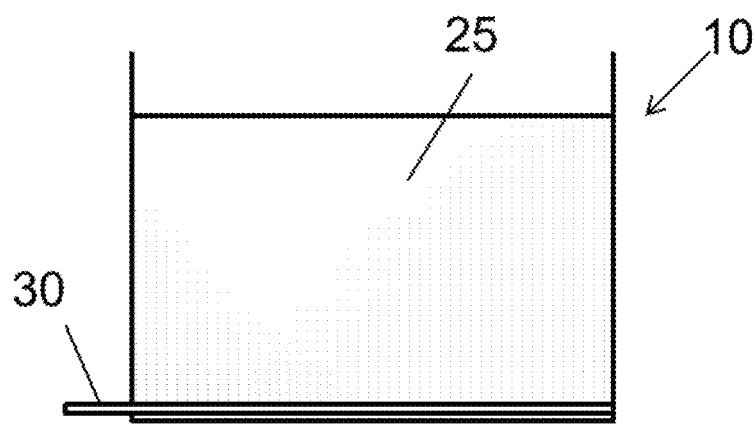
FIG. 1B illustrates another treatment stage of a sequencing batch reactor.

In the react stage (See FIG. 1B), the mixed liquor 25 may be provided with oxygen by aerators at the surface of the mixed liquor, for example, floating surface aerators (not shown), or by bubbling of oxygen-containing gas, for example, air, through the mixed liquor 25 from an aeration system 30. The oxygen is used by aerobic microbes to oxidize organic solids in the mixed liquor 25. In some embodiments, the SBR is operated under anoxic and/or anaerobic conditions, and no oxygen is introduced to the mixed liquor 25.

Figure 1C:
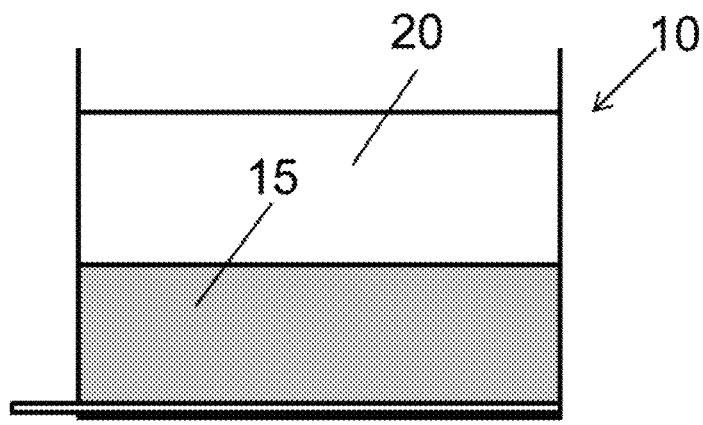
FIG. 1C illustrates another treatment stage of a sequencing batch reactor.

During the settle stage (See FIG. 1C) suspended solids in the mixed liquor 25 are allowed to settle by ceasing aeration or mechanical agitation of the mixed liquor. The suspended solids form a blanket of sludge 15 on the bottom of the SBR vessel 10 and a solids-lean supernatant 20 is formed above the sludge layer 15. As the term is used herein, a solids-lean supernatant is supernatant having a suspended solids level at or below an upper limit for environmental discharge of the supernatant in a jurisdiction in which the SBR is located. Microorganisms in the settled sludge 15 may use up substantially all oxygen in the sludge 15, providing for anaerobic processes, for example, denitrification to proceed in the settled sludge 15.

Figure 1D:
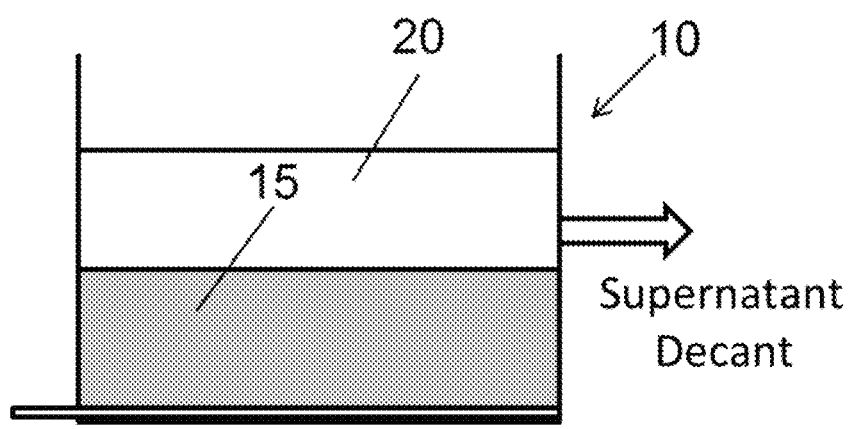
FIG. 1D illustrates another treatment stage of a sequencing batch reactor.

The solids-lean supernatant 20 is removed from the vessel during the decant stage (See FIG. 1D), for example, by opening an outlet valve of the vessel 10 or by pumping. In some embodiments, supernatant is removed from the surface or proximate the surface of the supernatant in the SBR vessel 10. The supernatant may be discharged to the environment or further treated, for example, to remove dissolved solids or chemical species if necessary to meet local regulations for environmental discharge.

Figure 1E:
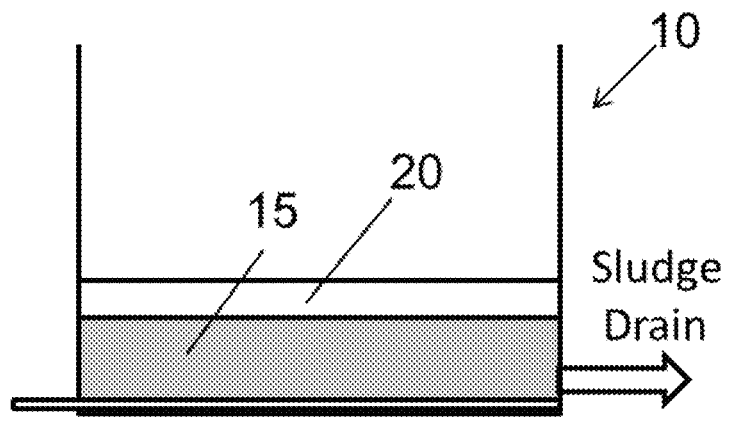
FIG. 1E illustrates another treatment stage of a sequencing batch reactor.

Settled sludge 15 may be removed from the vessel 10 as waste activated sludge (WAS) (See FIG. 1E) during or after the settle or decant stage, for example, by opening an outlet valve of the vessel 10 or by pumping. The WAS may be disposed of or further treated.

Figure 1F:
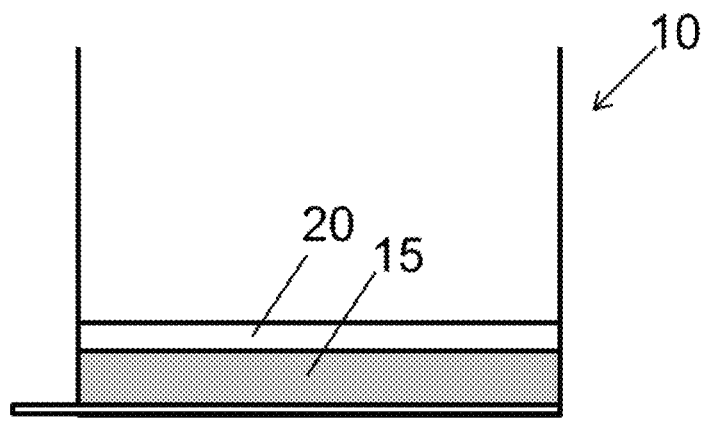
FIG. 1F illustrates another treatment stage of a sequencing batch reactor.

After the solids-lean supernatant 20 is removed from the SBR vessel, the SBR may enter an idle stage (See FIG. 1F) awaiting introduction of a next batch of wastewater. The SBR vessel 10 may include residual supernatant 20 and sludge 15 while in the idle stage.

The amount of time provided for the settle and decant stages in many existing SBR systems is typically fixed. Variations in process conditions, for example, liquid level in the SBR and type and amount of solids in the wastewater may result in either too much or too little supernatant and/or WAS being removed. If too much supernatant is removed, there is a risk that the level of supernatant in the SBR may be decreased to a point at which some suspended solids from the settled sludge may be removed with the supernatant. The decanted supernatant may thus exceed a maximum permitted suspended solids level and may require additional treatment or retreatment, resulting in an increase in treatment cost and time. Different municipalities may have different maximum allowable suspended solids levels for supernatant that is to be discharged into the environment for example, between 5 mg/L and 30 mg/L. If an amount of supernatant that is well below a volume that would result in a risk of decanting supernatant with an undesirably high suspended solids level is removed from the SBR vessel, the SBR would not be producing the amount of supernatant it was capable of, and would be running less efficiently than desired, reducing an amount of wastewater that could be treated or necessitating an increased number of SBRs in a wastewater treatment plant to accommodate a given wastewater flow. If too little WAS is removed the SBR vessel may accumulate an unnecessarily high level of solids, which may increase the time required to settle the solids and thus increase the SBR cycle time. If too much WAS is removed, an insufficient population of bacteria may remain in the SBR vessel to properly treat influent wastewater.

Aspects and embodiments disclosed herein are generally directed to an automated process of controlling solids-lean supernatant removal in a system supplied with varying quantities of wastewater by continually monitoring the liquid level and level of settling or settled solids in the system and to apparatus configured to perform such a process. Aspects and embodiments of this method and apparatus may be utilized in SBRs in which varying operating water levels are often encountered to optimize settling, idle, and decant cycles. The time for which suspended solids may take to settle from wastewater in an SBR may vary based on process conditions, for example, a concentration of solids in the wastewater, ambient temperature or temperature of liquid in the SBR, volume of wastewater introduced into the SBR, type and/or quantity of bacteria in the SBR, etc. The amount of solids-lean supernatant produced in an SBR and the time used to produce the solids-lean supernatant may also vary based on factors such as, for example, a concentration of solids in the wastewater, ambient temperature or temperature of liquid in the SBR, volume of wastewater introduced into the SBR, type and/or quantity of bacteria in the SBR, etc. Aspects and embodiments disclosed herein provide for the decanting of solids-lean supernatant from a SBR or other treatment system once solids have settled out from the supernatant to a desired degree by monitoring or measuring the amount of sludge settled to the bottom of the SBR and/or rate of sludge settling, rather than blindly relying on a pre-set time for the solids to settle. Aspects and embodiments disclosed herein provide for the decanting of an amount of solids-lean supernatant consistent with the amount of solids-lean supernatant actually produced from a batch of wastewater by monitoring or measuring the total liquid level and sludge level in an SBR or other treatment system and calculating the amount of available solids-lean supernatant instead of simply decanting for a pre-set time period. Systems disclosed herein may thus operate more efficiently than prior art systems by decanting solids-lean supernatant at a proper time and in a proper amount and/or rate to recover a greater amount of solids-lean supernatant having a desired low solids content than might be achievable by relying on fixed settling and decanting times. Systems disclosed herein may also or alternatively operate with a reduced cycle time as compared to conventional SBRs by performing the sludge settling and solids-lean supernatant decant stages at least partially concurrently.

In one embodiment, an automatic control system utilizes solids positioning sensors or switches to optimize solids-lean supernatant removal from a varying or fixed water level system. The solids positioning sensors or switches may be suspended solids sensors that are positioned at fixed locations within a wastewater treatment vessel, tank, or reactor. In another embodiment either single of multiple sensors or switches may be movable to various levels in a wastewater treatment vessel, tank, or reactor.

The solids positioning sensors or switches may include one or more ultrasonic sludge level sensors. The ultrasonic sludge level sensors may be operated at a frequency or frequencies that provides a desired level of precision and/or sensitivity for determining the position of an interface between settling or settled sludge and supernatant in the wastewater treatment vessel, tank, or reactor. It has been observed that ultrasonic level sensors operating at high frequencies, for example, above 750 kHz may not be capable of providing a reliable measurement of the position of a sludge blanket having low levels of suspended solids, such as those that might be present as the sludge has just begun to settle in an SBR. Ultrasonic level sensors operating at lower frequencies, for example, between 5 KHz and 800 KHz have been observed to be more capable of providing a reliable measurement of the position of a sludge blanket having low levels of suspended solids than ultrasonic level sensors operating at higher frequencies. Accordingly, in some embodiments, solids positioning sensors or switches utilized in the systems and methods disclosed herein may include one or more ultrasonic sludge level sensors that operate at a frequency of between about 5 KHz and about 800 KHz, between about 50 kHz and about 800 kHz, between about 50 kHz and about 200 kHz, or between about 200 kHz and 455 KHz. In some embodiments, solids positioning sensors or switches utilized in the systems and methods disclosed herein may include one or more ultrasonic sludge level sensors that operate at frequencies that commercially available ultrasonic transducers operate at, for example, 50 kHz, 200 kHz, 455 kHz, or 800 kHz, or combinations thereof.

In other embodiments, the solids positioning sensors or switches may include one or more CHIRP (Compressed High-Intensity Radar Pulse) sonar units. CHIRP sensors include a transducer that outputs a progressively increasing frequency in a specific range (for example, 28 kHz-60 kHz, 42 kHz-65 kHz, or 130 kHz-210 kHz) so a variety of frequencies are utilized to gain further resolution with regard to the depth and position of submerged objects as compared to ultrasonic level sensors operating at a single frequency.

In some embodiments, ultrasonic level sensors which continuously move with the varying water level are utilized. In some embodiments, ultrasonic level sensors, radar level sensors, floating level sensors, and/or fixed level sensors or switches may be used alone or in combination to detect both the solids level and the water level in a wastewater treatment vessel, tank, or reactor. One or more liquid level sensors may be used in combination with a solids position detecting instrument or sensor so that the solids level and the position of the supernatant/solids interface in a wastewater treatment vessel, tank, or reactor can be determined. The sensors or switches may be connected either with a cable or may be wirelessly connected to a control system and can be moored or mounted within the wastewater treatment vessel, tank, or reactor so that they may float and ride with the varying water levels.

When used in an SBR, the solids and liquid level or position sensors may profile the location of settling or settled solids and the interface between settling or settled solids and supernatant formed above the settling or settled solids. By knowing this information, it is possible to optimize the removal of solids-lean supernatant and/or the solids, for example, WAS from the wastewater treatment vessel, tank, or reactor. For example, a control system in communication with the liquid level and/or solids level sensors can trigger the start and stop of the solids-lean supernatant removal based on the relative level of liquid and settled solids in the wastewater treatment vessel, tank, or reactor. In another embodiment, a controller can control the rate of solids-lean supernatant removal based at least in part on, for example, a degree of sharpness of an interface between a sludge blanket and supernatant in the wastewater treatment vessel, tank, or reactor. In another embodiment, the sensors and control system can be used to trigger the start and stop of solids removal and can also control the rate at which the solids are removed.

In some embodiments, a "buffer layer" above the interface between a sludge blanket and supernatant in a vessel may be defined and solids-lean supernatant is removed from the vessel only at depths above the buffer layer. The thickness of the buffer layer may be determined based on the degree of sharpness of the interface between the sludge blanket and the supernatant. If the interface between the sludge blanket and the supernatant is not very sharp, decanting supernatant from a region close to the interface might risk decanting supernatant with an undesirably high concentration of suspended solids and so the buffer layer, or minimum depth above the sludge blanket from which supernatant should be decanted, may be defined with a greater depth than if the interface between the sludge blanket and the supernatant was more sharp. If the interface between the sludge blanket and the supernatant is very sharp, supernatant may be decanted from a position close to the interface between the sludge blanket and the supernatant with little risk of decanting supernatant with an undesirably high concentration of suspended solids and so the buffer layer, or minimum depth above the sludge blanket from which supernatant should be decanted, may be defined with a lesser depth than if the interface between the sludge blanket and the supernatant was less sharp.

In some embodiments, the control system may utilize data from the liquid level and/or solids level sensors to determine a degree of sharpness of an interface between a sludge blanket and supernatant in a wastewater treatment vessel and a desired minimum depth above the sludge layer or blanket from which supernatant should be decanted to avoid decanting supernatant with an undesirably high concentration of suspended solids. The control system may operate the wastewater treatment vessel or a decanting sub-system thereof to decant solids-lean supernatant from the vessel at a time and/or rate to maintain the level of supernatant in the vessel at or just above the desired minimum depth above the sludge layer or blanket during at least a portion or throughout substantially the entirety of the decant stage.

The degree of sharpness of an interface between a sludge blanket and supernatant in a wastewater treatment vessel may vary due to various factors, for example, changes in the content of wastewater introduced into the vessel, age of sludge in the vessel, changes in environmental conditions, for example, temperature, and/or changes to the types or quantity of bacteria present in the vessel (which may vary based on sludge age and/or temperature). Accordingly, the desired minimum depth above the sludge layer or blanket in a vessel from which supernatant should be decanted to avoid decanting supernatant with an undesirably high concentration of suspended solids may vary over time, for example, with seasons of the year. In some embodiments, the control system of the wastewater treatment vessel may utilize data from the liquid level and/or solids level sensors to periodically or continuously recalculate a degree of sharpness of an interface between a sludge blanket and supernatant in the vessel and the desired minimum depth above the sludge layer or blanket from which supernatant should be decanted to avoid decanting supernatant with an undesirably high concentration of suspended solids to account for changes over time in the degree of sharpness of the interface between the sludge blanket and the supernatant. The controller may utilize the recalculated value of the desired minimum depth above the sludge layer or blanket from which supernatant should be decanted to avoid decanting supernatant with an undesirably high concentration of suspended solids to periodically or continuously adjust the time and/or rate of solids-lean supernatant decanting to maintain the level of supernatant in the vessel at or just above the recalculated desired minimum depth above the sludge layer or blanket during at least a portion or throughout substantially the entirety of the decant stage.

In some embodiments, the system may be operated in batch mode with non-predetermined and varying quantities of wastewater introduced to the wastewater treatment vessel, tank, or reactor at unknown and varying flow rates.

In some embodiments, a ballast material, for example, magnetite or other high density material may be added to the wastewater treatment vessel, tank, or reactor to enhance the settling rate of the solids.

Aspects and embodiments disclosed herein are not limited to being used in an SBR and may be used in aerobic and/or anaerobic digesters to optimize thickening and waste cycles from these tanks. Aspects and embodiments disclosed herein are not limited to the type, number, location and combination of sensors or switches used.

In some embodiments, a wastewater treatment system includes a wastewater treatment vessel, tank, or reactor equipped with a system to determine and/or continuously monitor an overall liquid level as well as a depth or level of a blanket of settling or settled sludge in the vessel, tank, or reactor. The terms "vessel," "tank," and "reactor" are used synonymously herein and should be understood to encompass SBRs. The system may be further configured to determine a change in concentration of suspended solids with depth in the vessel and to quantify a degree of sharpness of an interface between settled or settling sludge and a supernatant in the vessel. As the term is used herein, a degree of sharpness of a solids/liquid or solids/supernatant interface is defined by a change in suspended solids concentration with depth across the interface. As the terms are used herein low-solids supernatant, solids-lean supernatant, or simply supernatant is wastewater in a wastewater treatment vessel from which solids have been at least partially removed, for example, by settling. Typically, when wastewater including suspended solids is left in a wastewater treatment vessel under quiescent conditions solids having a specific gravity greater than water will settle to the bottom of the vessel over time resulting in a sludge "blanket" on the bottom of the vessel covered by a layer of low-solids supernatant, for example, low-solids water. The term "low-solids" is a relative term used herein to characterize supernatant as opposed to solids-rich sludge in a wastewater treatment vessel.

A liquid and sludge level monitoring system may include one or more sensors. In some embodiments one type of sensor may be utilized to monitor or measure the overall liquid level in the vessel and another type of sensor may be utilized to monitor or measure a level or depth of a layer of sludge or an interface between sludge and supernatant in the vessel. The overall liquid level in the vessel typically will correspond with the upper surface of the supernatant in the vessel. In other embodiments, similar or the same types of sensors may monitor or measure the overall liquid level in the vessel and the level or depth of a layer of sludge or an interface between sludge and supernatant in the vessel. In further embodiments, the same sensor may monitor or measure the overall liquid level in the vessel and the level or depth of a layer of sludge or an interface between sludge and supernatant in the vessel.

The level or depth sensors of the liquid and sludge level monitoring system may be in wired or wireless communication with a controller of the wastewater vessel and may communicate data including indications of measured liquid or sludge levels, depths, or suspended solids or sludge concentrations to the controller. The controller may be programmed to control various operating parameters of the vessel, for example, timing or rate of introduction of wastewater to the vessel, timing or rate of removal of supernatant or sludge from the vessel, timing or rate or aeration or mixing of the vessel, or any other operating parameters of interest based at least partially on data received from one or more of the sensors.

Figure 2:
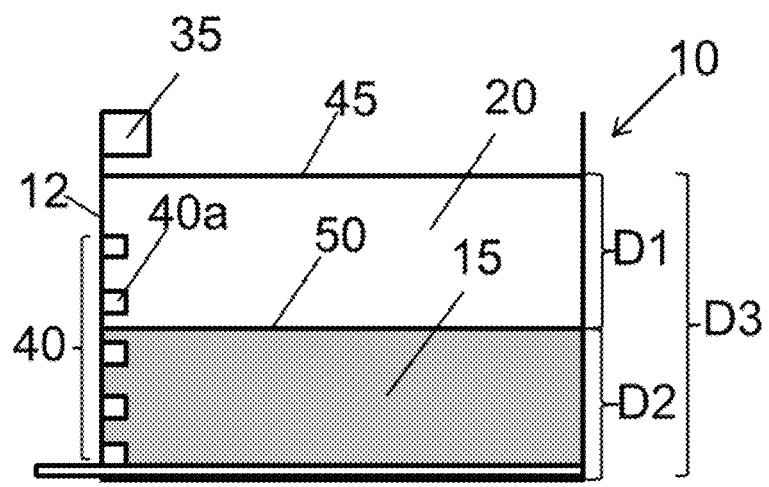
FIG. 2 illustrates an embodiment of a wastewater treatment vessel.

In one embodiment, illustrated in FIG. 2, a wastewater treatment vessel 10 includes an overall liquid level or supernatant level sensor 35 and a sludge level/suspended solids concentration sensor 40. The sludge level/suspended solids concentration sensor 40 (hereinafter the "sludge sensor") includes a plurality of sensor elements 40a fixed in place on a wall 12 of the vessel 10. The sludge sensor 40, or a controller with which the sludge sensor 40 communicates, may determine a location of a top 50 of a layer of sludge 15 (also referred to herein as the interface between the sludge layer 15 and the supernatant 20) by comparing measurements of suspended solids concentration provided by the different sensor elements 40a. The sludge sensor 40 may also be used to determine a degree of sharpness of the interface between the sludge layer 15 and the supernatant 20 by providing an indication of how the level of suspended solids changes from one sensor element 40a to the next, and hence how the concentration of suspended solids changes with depth.

Figure 3:
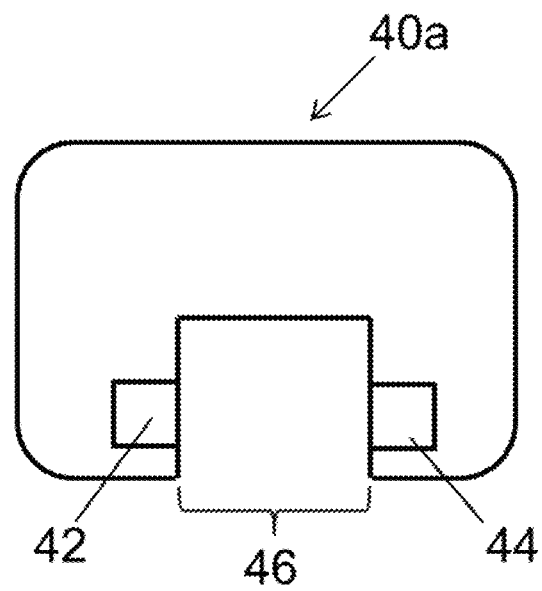
FIG. 3 illustrates and embodiment of a sensor element utilized in the wastewater treatment vessel of FIG. 2.

The sensor elements 40a of the sludge sensor 40 may include, for example, optical (e.g., infrared) or ultrasonic sensors. In one example, illustrated in FIG. 3, the sensor elements 40a of the sludge sensor 40 may include a signal transmitter 42 (e.g., an infrared light emitter or an ultrasonic transducer) and a signal receiver 44 (e.g., an infrared or ultrasound receiver) separated by a gap 46 from the signal transmitter 42. Liquid in a vessel in which the sensor element 40a is disposed fills the gap 46 between the signal transmitter 42 and signal receiver 44. The sensor elements 40a may provide output signals indicative of a degree of attenuation of the signal (the infrared light or ultrasound) from the signal emitter 42 that is received at the signal receiver 44. The degree of attenuation of the signal may be correlated with suspended solids concentration or turbidity of the liquid in the vessel 10. The difference in signal attenuation at the different sensor elements 40a of the sludge sensor 40 of FIG. 2 can be used to determine a profile of suspended solids or sludge concentration versus depth in the vessel 10 and thus may be used to determine a position and/or degree of sharpness of the sludge/supernatant interface 50. The sensor elements 40a of the sludge sensor 40 are not limited to being optical or ultrasonic sensors and may include any type of sensor capable of providing a signal indicative of a concentration of suspended solids or sludge at locations in the vessel 10. More or fewer sensor elements 40a than illustrated, for example, 64 or more sensor elements 40a may be provided. The sensor elements 40a of the sludge sensor 40 may be disposed on a single wall 12 of the vessel 10 as illustrated or on more than one wall. The sensor elements 40a may include wipers (not shown in FIG. 3) or other self-cleaning mechanisms to remove foulants from the signal transmitter 42 and/or signal receiver 44 as desired.

The sensor elements 40a may additionally or alternatively be utilized to sense a level of liquid in the vessel 10. If a signal passing from a signal transmitter 42 to a signal receiver 44 in a first sensor element 40a above a second sensor element 40a is not attenuated, or not significantly attenuated, while the signal passing from the signal transmitter 42 to the signal receiver 44 in the second sensor element 40a is attenuated significantly more than that of the first sensor element 40a, it can be concluded that the liquid surface is between the first and second sensor elements.

The overall liquid level or supernatant level sensor 35 may also be fixed in place on a wall 12 of the vessel, which may be the same or a different wall than that to which the sludge sensor 40 is attached. The overall liquid level or supernatant level sensor 35 may alternatively be suspended by a pole, cable, scaffold, or other mechanism above the surface of liquid in the vessel 10. The sensor 35 may be an ultrasonic sensor, a radar sensor, an optical sensor, or any other type of sensor capable of providing an indication of the height or level of the top surface 45 of the supernatant 20 or wastewater in the vessel 10. In some embodiments, for example, the embodiment illustrated in FIG. 2, the level sensor 35 may be disposed at a position above an expected upper level of liquid in the vessel 10.

Together, the sludge sensor 40 and level sensor 35 may be used to determine a supernatant depth D1, a sludge layer thickness or depth D2, and an overall liquid depth D3 in the vessel 10. In some embodiments, the supernatant depth D1 and/or depth of the sludge/supernatant interface is determined by a controller by subtracting a sludge layer thickness D2 determined from an output of the sludge sensor 40 from the liquid level D3 determined from an output of level sensor 35.

Figure 4:
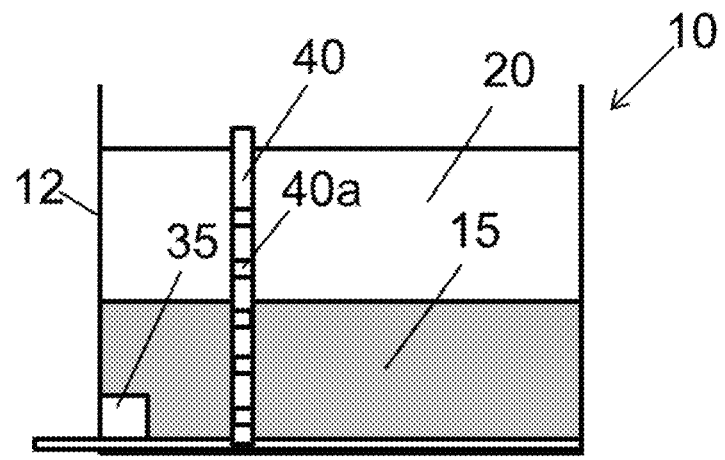
FIG. 4 illustrates another embodiment of a wastewater treatment vessel.

In another embodiment, illustrated in FIG. 4, the sludge sensor 40 includes an elongate element, for example, a rod, pole, or cable that is mounted in the vessel 10 at a position displaced from walls 12 of the vessel. Sensor elements 40a, which may be similar in construction and operation to sensor elements 40a discussed with regard to the embodiment illustrated in FIG. 2 may be disposed at different positions along the length of the elongate element, and thus at different depths in the vessel 10. In one particular example, the sludge sensor 40 may be similar to the Automated Sludge Blanket Level Detector available from Markland Specialty Engineering Ltd., having 64 photodetector sensor elements over a length of four feet (1.2 meters).

The liquid level sensor 35 illustrated in FIG. 4 is a liquid pressure sensor. As the level of liquid in the vessel 10 increases, the liquid pressure at the bottom of the vessel 10 increases. The liquid level sensor 35 illustrated in FIG. 4 is configured to measure or monitor the liquid pressure at the bottom of the vessel 10 or proximate the bottom of the vessel 10 and provide data including an indication of the pressure to a controller that can determine the level of liquid (wastewater or sludge and supernatant) in the vessel based on the indication of the pressure. The liquid level sensor 35 is illustrated in FIG. 4 adjacent to a wall 12 of the vessel, but in different embodiments may be disposed in alternate locations.

Figure 5:
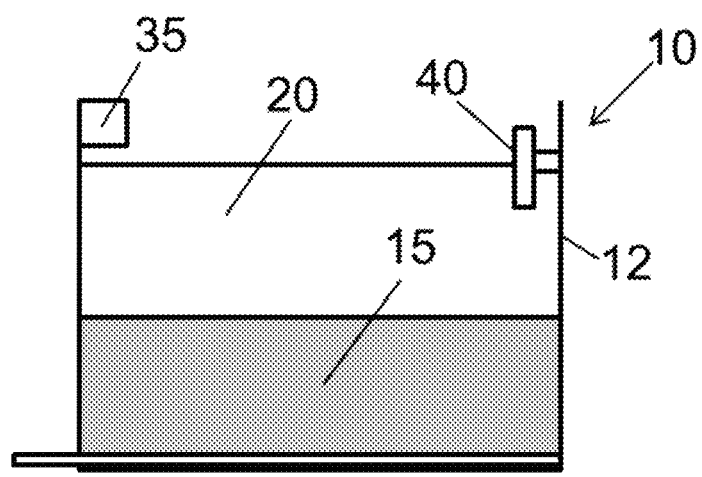
FIG. 5 illustrates an embodiment of a wastewater treatment vessel.

In the embodiment illustrated in FIG. 5, the level sensor 35 is similar in construction and operation to the level sensor 35 illustrated in FIG. 2. The sludge sensor 40 in the embodiment illustrated in FIG. 5 extends at least partially into the liquid in the vessel 10. The sludge sensor 40 of FIG. 5 may include, for example, an ultrasonic transceiver or separate transmitter and receiver. The speed of travel of ultrasound pulses emitted from the ultrasonic transceiver may be different in wastewater, low-solids supernatant 20, and sludge 15. The sludge sensor 40 of FIG. 5 may measure a time between emission of an ultrasonic pulse and receipt of an echo of the ultrasonic pulse to determine the amount of sludge 15 in the vessel 10 and thus the height of the blanket of sludge 15. In some embodiments, a controller may utilize knowledge of a positon of the sludge sensor 40 in a calculation of the height of the blanket of sludge 15 and/or depth of the sludge/supernatant interface calculated from data provided from the sludge sensor 40. For example, if the sludge sensor 40 is positioned above X meters of liquid in the vessel 10, and if it would be expected to take Y milliseconds for an ultrasound pulse emitted from the sludge sensor 40 to echo off the bottom of the vessel and return to the sludge sensor 40 if the vessel was filled with low-solids supernatant, the controller could compare an actual amount of time Z between pulse emission and echo detection to time Y in view of the expected speed of travel of the ultrasound pulse through low-solids supernatant and sludge to determine the height of the blanket of sludge 15. In some embodiments, the sludge sensor 40 may be similar to the SONATAX™ sc Sludge Blanket Level Probe available from the Hach Company. The sludge sensor 40 of FIG. 5 may include a wiper (not shown in FIG. 5) or other self-cleaning mechanism to remove foulants from the its signal transmitter, receiver, or transceiver as desired.

Figure 6:
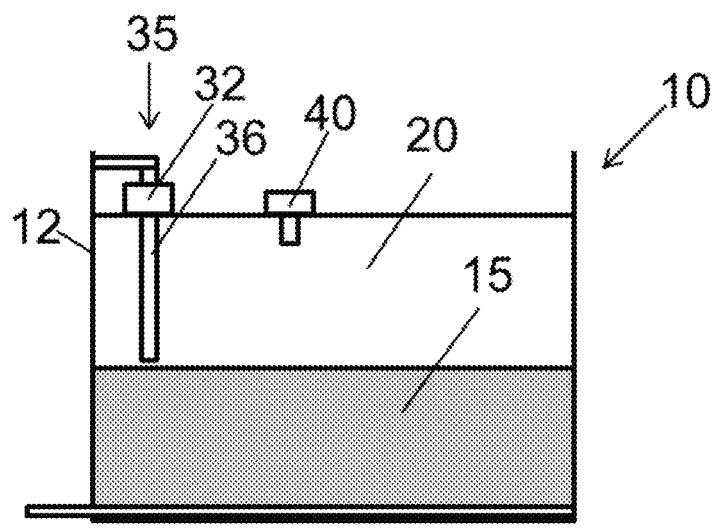
FIG. 6 illustrates an embodiment of a wastewater treatment vessel.

FIG. 6 illustrates an embodiment in which both the level sensor 35 and the sludge sensor 40 include floating elements that move vertically with the level of liquid in the vessel 10. The level sensor 35 of the embodiment of FIG. 6 is a float sensor including a float 32 mounted on a rod 36. The rod 36 may be secured to a wall 12 of the vessel 10 or otherwise secured in place within the vessel 10. The float 32 includes one or more magnets and the rod 36 includes one or more magnetic sensors, for example, reed switches, at known locations along its length. As the liquid level in the vessel 10 varies the float 32 moves up and down about the rod 36. As the one or more magnets in the float 32 approach a magnetic sensor in the rod 36, the magnetic sensor can provide a signal to a controller which can interpret the signal to determine the position of the float 32 and thus the level of liquid in the vessel 10.

The sludge sensor 40 of FIG. 6 may include, for example, an ultrasonic transceiver or separate transmitter and receiver mounted on a float. The sludge sensor 40 of FIG. 6 may float on the liquid in the vessel 10 and rise and fall with the overall liquid level in the vessel 10. The sludge sensor 40 of FIG. 6 may operate in a similar manner as the sludge sensor 40 of FIG. 5 described above. In some embodiments, a controller may utilize data received from the level sensor 35 regarding the total level of liquid in the vessel 10 to refine a calculation of the height of the blanket of sludge 15 and/or depth of the sludge/supernatant interface calculated from data provided from the sludge sensor 40. For example, if the data received from the level sensor 35 indicates that there is D3 meters of liquid in the vessel 10, and if it would be expected to take X milliseconds for an ultrasound pulse emitted from the sludge sensor 40 to echo off the bottom of the vessel and return to the sludge sensor 40 if the vessel was filled with low-solids supernatant, the controller could compare an actual amount of time Y between pulse emission and echo detection to time X in view of the expected speed of travel of the ultrasound pulse through low-solids supernatant and sludge to determine the height of the blanket of sludge 15. The floating sludge sensor 40 of FIG. 6 may be operable at a greater range of liquid levels than, for example, the sludge sensor 40 of FIG. 5 which might be disposed outside of the liquid in the vessel if the liquid level fell too far. Further, a floating sludge sensor may be operable to measure more shallow layers of supernatant than a fixed sludge sensor. A floating sludge sensor may, for example, be used in a control system configured to remove or decant supernatant during the settling stage of an SBR cycle. The supernatant may be decanted while maintaining only a depth of supernatant, for example, about six inches (15.2 cm) sufficient to provide decanted solids-lean supernatant with a desired low solids concentration. The suspended solids level of the decanted solids-lean supernatant may be controlled or minimized by providing a sufficient supernatant depth above the supernatant/sludge interface to avoid decanting sludge or suspended solids from a mixing layer around the supernatant/sludge interface which may include an undesirably high amount of suspended solids. The sludge sensor 40 of FIG. 6 may include a wiper (not shown in FIG. 6) or other self-cleaning mechanism to remove foulants from the its signal transmitter, receiver, or transceiver as desired. In further embodiments, a sludge sensor including an ultrasonic transducer may be built into the float 32 of the level sensor 35 to produce a combination liquid level sensor/sludge depth sensor and separate sludge sensor 40 may be omitted.

Figure 7:
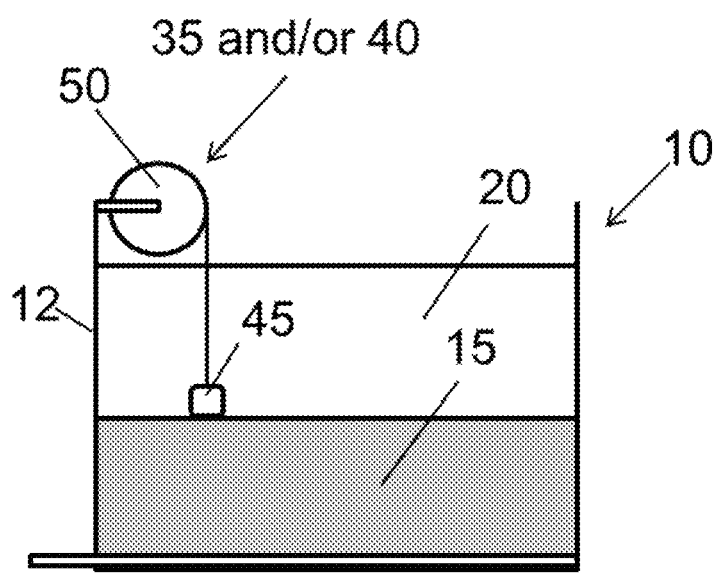
FIG. 7 illustrates an embodiment of a wastewater treatment vessel.

In another embodiment, illustrated in FIG. 7, a sludge sensor 40 and/or level sensor 35 may include a submersible element 45 suspended by a cable in the liquid in the vessel 10. A winch 50 may be utilized to drop the submersible element 45 to different depths within the vessel and may include a sensor to track the depth to which the submersible element 45 has been dropped. In one embodiment, the submersible element 45 may include a suspended solids concentration monitor having optical or ultrasonic signal transmitters and receivers, similar to the sensor element 40a illustrated in FIG. 3. In another embodiment, the submersible element 45 may additionally or alternatively include a liquid level sensor, for example a pressure sensor to provide an indication of a depth of the submersible element 45 below a surface of liquid in the vessel 10. Additionally or alternatively, the submersible element 45 may have a density intermediate between that of the supernatant 20 and the sludge 15 in the vessel. The submersible element 45 may be lowered by the winch 50 into the liquid in the vessel until it comes to rest and floats on the surface of the layer of sludge 15 beneath the supernatant 20, thereby providing an indication of a depth of the sludge/supernatant interface. The submersible element 45 and/or winch 50 may provide data indicative of the level of liquid in the vessel, the depth of the sludge/supernatant interface or height of the sludge layer, and/or a profile of suspended solids concentration versus depth to a controller of the vessel 10.

Data regarding the level of liquid in the vessel 10 and the depth of the sludge/supernatant interface or height of the sludge layer provided by any of the level sensors and sludge sensors disclosed herein may be utilized by a control system to control operation of the vessel 10. For example, an indication of suspended solids concentration in wastewater introduced into the vessel provided by an embodiment of one of the sensors disclosed herein may be utilized by the control system to determine a desired amount or time of aeration or mixing or to estimate a desired solids settling time. An indication of a degree of sharpness of the sludge/supernatant interface provided by an embodiment of one of the sensors disclosed herein may be utilized by the control system to determine when to begin decanting solids-lean supernatant. Decanting of solids-lean supernatant may be initiated by the control system once the sludge/supernatant interface exhibits a desired degree of sharpness so that a solids-lean supernatant having a desirably low amount of suspended solids may be decanted.

An indication of the degree of sharpness of the sludge/supernatant interface provided by an embodiment of one of the sensors disclosed herein may be utilized by the control system to determine how quickly to decant solids-lean supernatant from the vessel. The control system may initiate decanting of solids-lean supernatant while solids are still in the process of settling from the wastewater/supernatant. The control system may first decant the solids-lean supernatant slowly so solids-rich supernatant lower in the vessel is not decanted until the solids in the solids-rich supernatant settle out. The rate of solids-lean supernatant decanting may be increased by the control system as the sludge/supernatant interface becomes sharper as there will be more confidence that supernatant decanted from the vessel will not contain an undesirable concentration of solids.

An indication of a depth of the sludge/supernatant interface provided by an embodiment of one of the sensors disclosed herein may be utilized by the control system to determine how much solids-lean supernatant may be decanted without risking decanting sludge along with the solids-lean supernatant. An indication of a depth of the sludge/supernatant interface provided by an embodiment of one of the sensors disclosed herein may be utilized by the control system to determine when and how much sludge to drain or waste from the vessel 10 to provide a desired amount of sludge (and microorganisms) in the vessel. An indication of the degree of sharpness of the sludge/supernatant interface provided by an embodiment of one of the sensors disclosed herein may be utilized by the control system to determine how quickly to drain or waste sludge from the vessel 10. If the sludge/supernatant interface is not sharp, it may be desirable to drain the sludge from the vessel 10 at a relatively slow first rate so as not to introduce turbulence into the vessel that may remix the sludge and supernatant. If the sludge/supernatant interface is sharp it may be desirable to drain the sludge from the vessel 10 at a relatively higher second rate that is higher than the first rate so that the sludge is removed before it can remix with the supernatant.

Various operating parameters of the wastewater treatment vessels or SBRs disclosed herein may be controlled or adjusted by an associated control system or controller based on various parameters measured by various sensors located in different portions of the vessels. The controller used for monitoring and controlling operation of the various elements of a vessel 10 or a wastewater treatment system including a vessel 10 may include a computerized control system. Various aspects of the controller may be implemented as specialized software executing in a general-purpose computer system 100 such as that shown in FIG. 8. The computer system 100 may include a processor 102 connected to one or more memory devices 104, such as a disk drive, solid state memory, or other device for storing data. Memory 104 is typically used for storing programs and data during operation of the computer system 100. Components of computer system 100 may be coupled by an interconnection mechanism 106, which may include one or more busses (e.g., between components that are integrated within a same machine) and/or a network (e.g., between components that reside on separate discrete machines). The interconnection mechanism 106 enables communications (e.g., data, instructions) to be exchanged between system components of system 100. Computer system 100 also includes one or more input devices 108, for example, a keyboard, mouse, trackball, microphone, touch screen, and one or more output devices 110, for example, a printing device, display screen, and/or speaker. In addition, computer system 100 may contain one or more interfaces (not shown) that connect computer system 100 to a communication network in addition or as an alternative to the interconnection mechanism 106.

The output devices 110 may also comprise valves, pumps, or switches which may be utilized to introduce wastewater into a treatment vessel, mix or aerate the wastewater in the vessel, and/or remove supernatant or sludge from the vessel. The one or more input devices 108 may also include any of the liquid level or sludge sensors disclosed herein.

Figure 9:
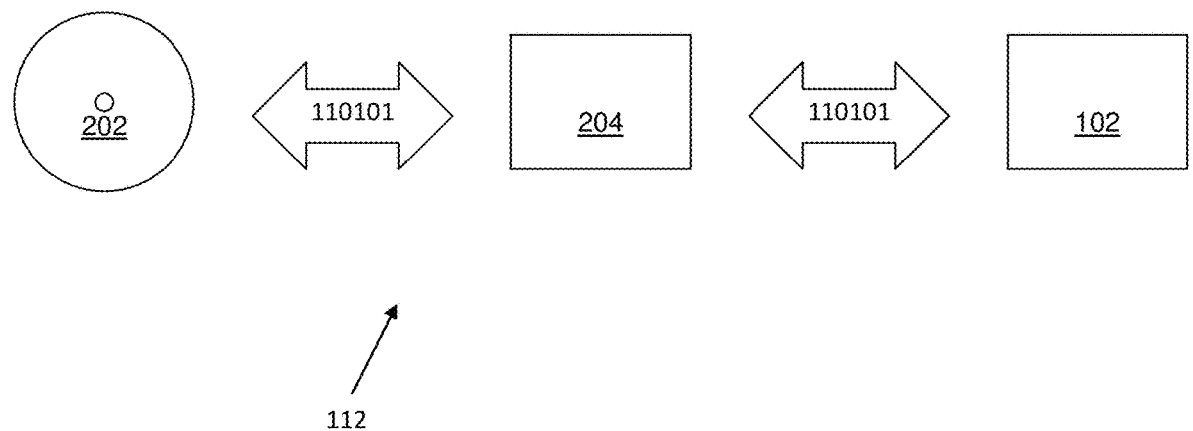
FIG. 9 illustrates a memory system for the control system of FIG. 8.

The storage system 112, shown in greater detail in FIG. 9, typically includes a computer readable and writeable non-volatile recording medium 202 in which signals are stored that define a program to be executed by the processor 102 or information to be processed by the program. The medium may include, for example, a disk or flash memory. Typically, in operation, the processor causes data to be read from the nonvolatile recording medium 202 into another memory 204 that allows for faster access to the information by the processor than does the medium 202. This memory 204 is typically a volatile, random access memory such as a dynamic random access memory (DRAM) or static memory (SRAM). It may be located in storage system 112, as shown, or in memory system 104. The processor 102 generally manipulates the data within the integrated circuit memory 204 and then copies the data to the medium 202 after processing is completed. A variety of mechanisms are known for managing data movement between the medium 202 and the integrated circuit memory element 204, and aspects and embodiments disclosed herein are not limited thereto. Aspects and embodiments disclosed herein are not limited to a particular memory system 104 or storage system 112.

The computer system may include specially-programmed, special-purpose hardware, for example, an application-specific integrated circuit (ASIC). Aspects and embodiments disclosed herein may be implemented in software, hardware or firmware, or any combination thereof. Further, such methods, acts, systems, system elements and components thereof may be implemented as part of the computer system described above or as an independent component.

Figure 8:
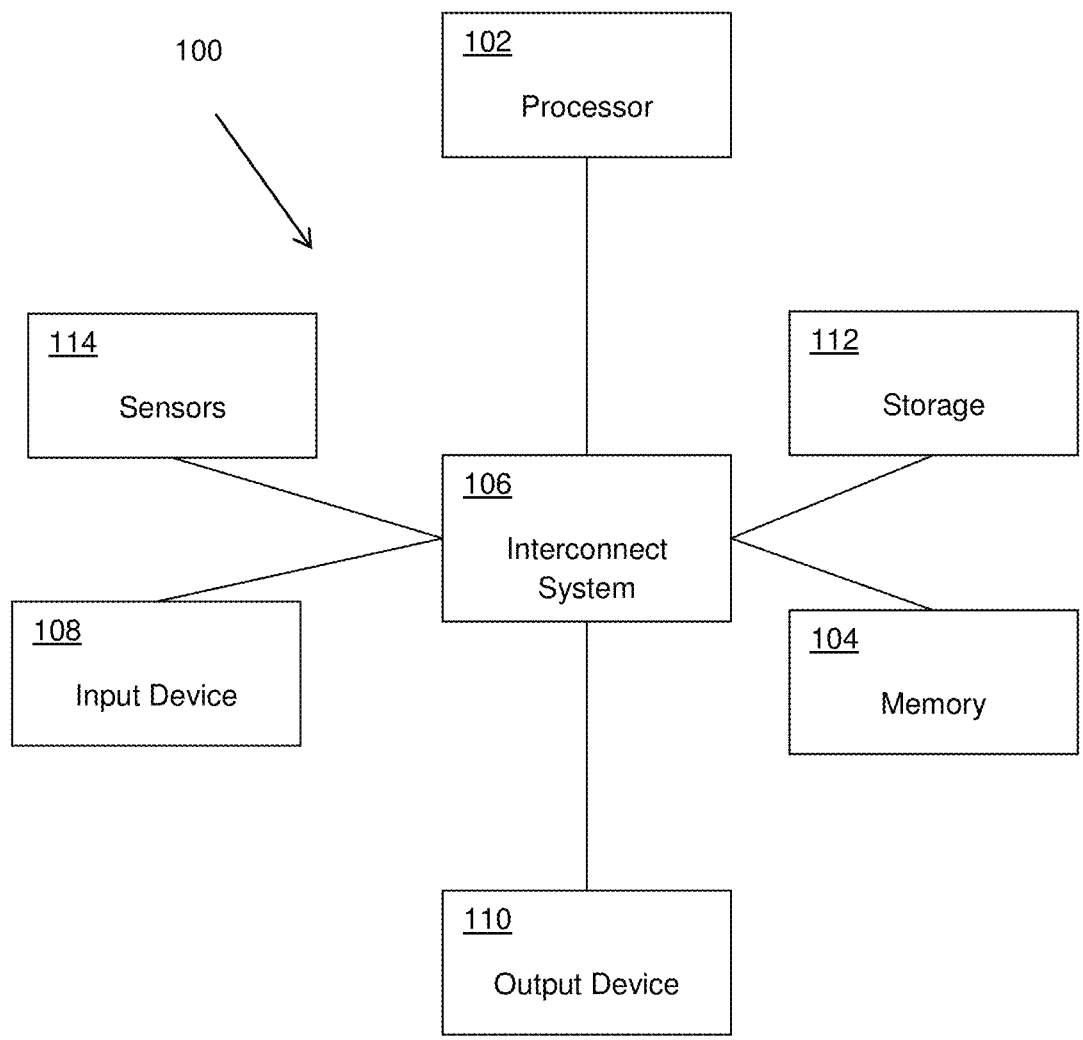
FIG. 8 illustrates a control system for embodiments disclosed herein.

Although computer system 100 is shown by way of example as one type of computer system upon which various aspects and embodiments disclosed herein may be practiced, it should be appreciated that aspects and embodiments disclosed herein are not limited to being implemented on the computer system as shown in FIG. 8. Various aspects and embodiments disclosed herein may be practiced on one or more computers having a different architecture or components that that shown in FIG. 8.

Computer system 100 may be a general-purpose computer system that is programmable using a high-level computer programming language. Computer system 100 may be also implemented using specially programmed, special purpose hardware. In computer system 100, processor 102 is typically a commercially available processor such as the well-known Pentium™, Lore™, or Atom™ class processors available from the Intel Corporation. Many other processors are available, including programmable logic controllers. Such a processor usually executes an operating system which may be, for example, the Windows 7, Windows 8, or Windows 10 operating system available from the Microsoft Corporation, the MAC OS System X available from Apple Computer, the Solaris Operating System available from Sun Microsystems, or UNIX available from various sources. Many other operating systems may be used.

The processor and operating system together define a computer platform for which application programs in high-level programming languages are written. It should be understood that the invention is not limited to a particular computer system platform, processor, operating system, or network. Also, it should be apparent to those skilled in the art that aspects and embodiments disclosed herein are not limited to a specific programming language or computer system. Further, it should be appreciated that other appropriate programming languages and other appropriate computer systems could also be used.

One or more portions of the computer system may be distributed across one or more computer systems (not shown) coupled to a communications network. These computer systems also may be general-purpose computer systems. For example, various aspects of the invention may be distributed among one or more computer systems configured to provide a service (e.g., servers) to one or more client computers, or to perform an overall task as part of a distributed system. For example, various aspects and embodiments disclosed herein may be performed on a client-server system that includes components distributed among one or more server systems that perform various functions according to various aspects and embodiments disclosed herein. These components may be executable, intermediate (e.g., IL) or interpreted (e.g., Java) code which communicate over a communication network (e.g., the Internet) using a communication protocol (e.g., TCP/IP). In some embodiments one or more components of the computer system 100 may communicate with one or more other components over a wireless network, including, for example, a cellular telephone network.

It should be appreciated that the aspects and embodiments disclosed herein are not limited to executing on any particular system or group of systems. Also, it should be appreciated that the aspects and embodiments disclosed herein are not limited to any particular distributed architecture, network, or communication protocol. Various aspects and embodiments disclosed herein are may be programmed using an object-oriented programming language, such as SmallTalk, Java, C++, Ada, or C# (C-Sharp). Other object-oriented programming languages may also be used. Alternatively, functional, scripting, and/or logical programming languages may be used, for example ladder logic. Various aspects and embodiments disclosed herein are may be implemented in a non-programmed environment (e.g., documents created in HTML, XML or other format that, when viewed in a window of a browser program, render aspects of a graphical-user interface (GUI) or perform other functions). Various aspects and embodiments disclosed herein may be implemented as programmed or non-programmed elements, or any combination thereof.

Example 1: Measurement System Performance

To illustrate the variability in liquid level and sludge levels between cycles in an SBR, liquid level and sludge level sensors were installed in an SBR in a wastewater treatment facility and measurements of the liquid levels and sludge levels were taken over a period of two days. The liquid level sensor was a SITRANS LU™ ultrasonic level sensor model number 7ML522-2AA18 from Siemens AG. The liquid level sensor was disposed 17 feet, 3 inches (5.26 meters) from above the bottom of the SBR vessel, well above the upper level of liquid reached in the vessel during testing, which was about 11 feet (3.35 meters). The sludge level sensor was a SONATAX™ sc Sludge Blanket Level Probe from the Hach Company. The sludge level sensor was mounted on floats and the ultrasonic transceiver of the sludge level sensor extended between 3 and 8 inches (between 7.6 cm and 20.3 cm) below the surface of the liquid in the SBR. Measurements were taken using the liquid level sensor and sludge sensor during normal operation of the SBR with a 2.5 hour timed fill stage, a one hour timed react stage, a one hour timed settle stage, and a 25 minute timed decant/idle stage.

Figure 10:
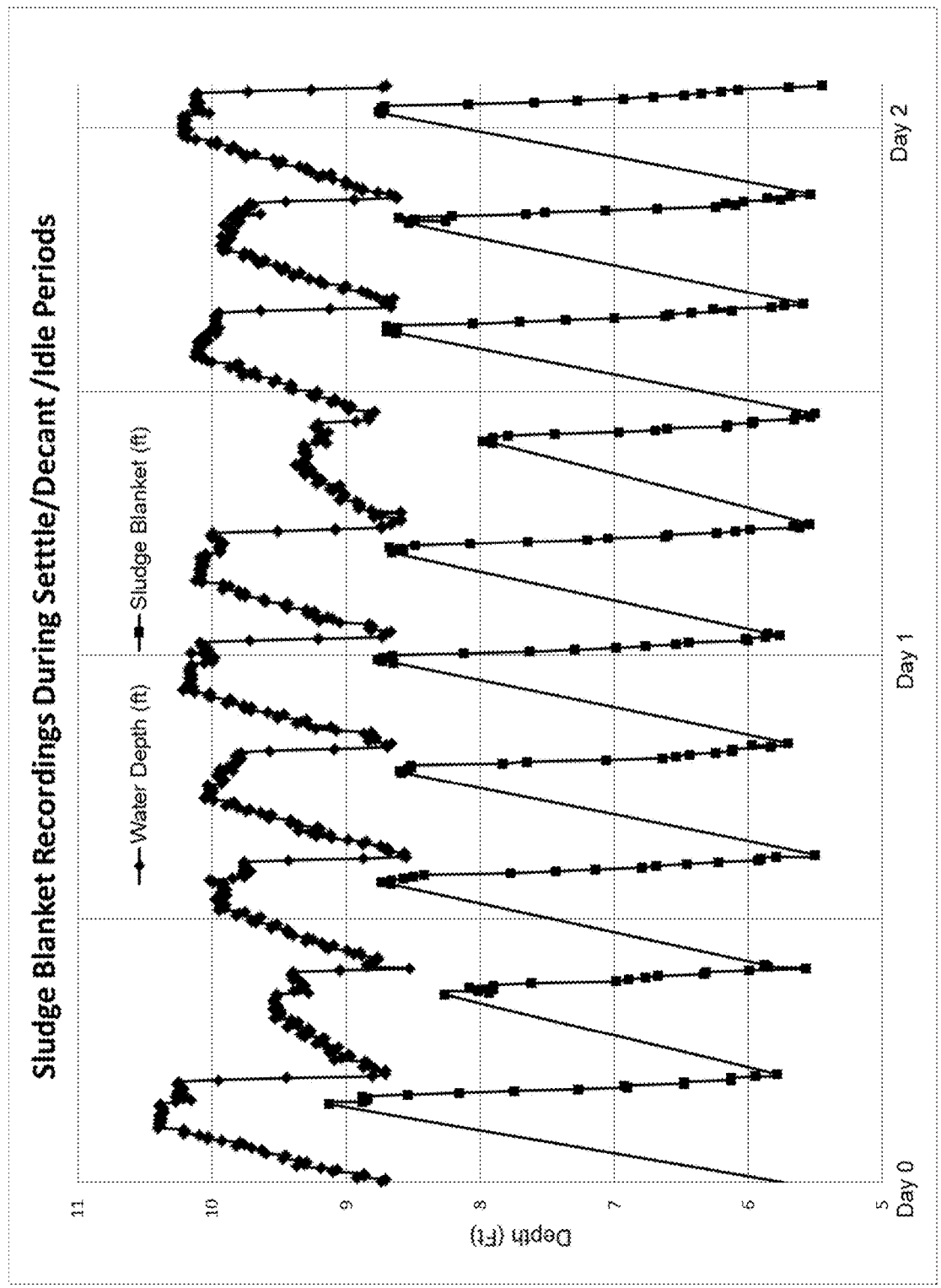
FIG. 10 illustrates levels of liquid and sludge in a Sequencing Batch Reactor measured over time with embodiments of a sensor system disclosed herein.

As can be seen in FIG. 10, over the period of two days, the liquid and sludge levels in the SBR varied from cycle to cycle and were not pre-determined. The liquid level varied at the end of each fill cycle (the peaks in the water depth curve) between about 9.3 feet and about 10.5 feet. The sludge level at the end of each fill cycle varied from about eight feet to just over nine feet. At the end of each decant cycle the liquid level dropped to about 8.5 feet, with some variation between cycles, and the sludge level dropped to between about 5.5 feet and about 5.8 feet.

Example 2: Measurement Accuracy

Figure 11:
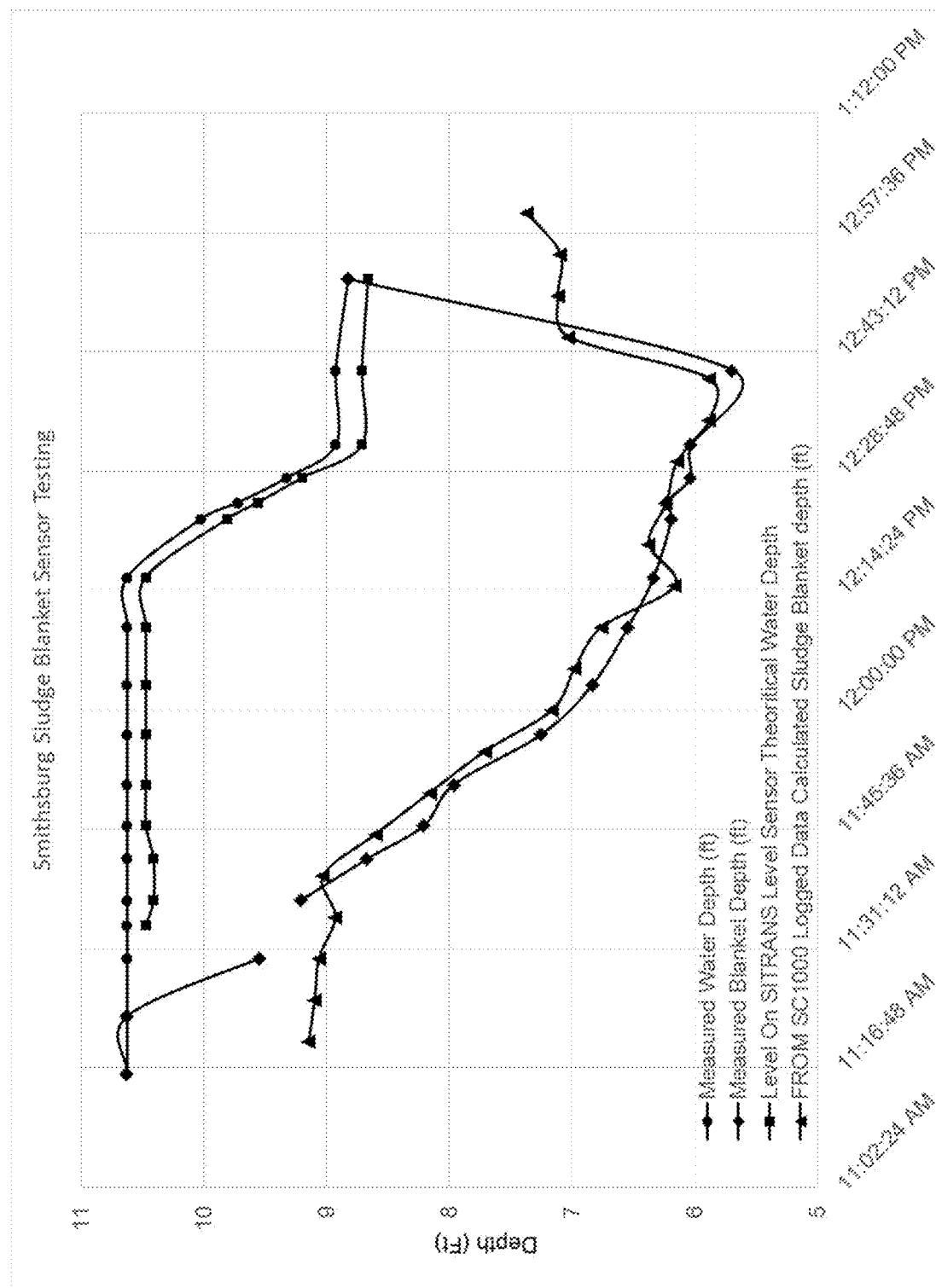
FIG. 11 illustrates a comparison of sensor depth measurements to manual measurements of liquid and sludge depth.

The accuracy of the SITRANS LU™ ultrasonic level sensor and of the SONATAX™ sc Sludge Blanket Level Probe for measuring liquid level and sludge level, respectively, was examined by comparing the readings from these sensors to manually made physical measurements of the liquid and sludge levels during the settle and decant stages of one cycle of the same SBR used in Example 1. FIG. 11 illustrates a comparison between the sensor readings and the physical measurements of liquid level and sludge depth. As can be seen from this data, aside from some discrepancies in the sludge blanket depth at the beginning of the settle stage and the end of the decant stage, the sensor measurements closely matched the physically observed liquid and sludge levels. Without being bound to a particular theory it is believed that these discrepancies were due to the SONATAX™ sc Sludge Blanket Level Probe utilizing an operating frequency that rendered it unable to accurately determine the level of the low solids concentration sludge blanket at the beginning of the settle stage, and at the end of the decant stage when mixing of the liquid in the SBR began. This data illustrates that the sensors utilized may be used to accurately measure liquid level and sludge depth throughout at least a majority of an operating cycle in an SBR.

Example 3: Prophetic Amount of Cycle Time Savings

A control system of an SBR may be configured to begin decanting solids-lean supernatant during the settle stage of an SBR once the sludge/supernatant interface has dropped to a depth, for example, between about six inches (15.24 cm) and about three feet (91.4 cm) below the surface of the liquid in the SBR. This depth may be selected based on the degree of sharpness of the supernatant/sludge interface so that solids-lean supernatant having a desired low solids content, for example, a suspended solids content below that required for environmental discharge of the supernatant by regulations in a region in which the wastewater treatment system including the SBR is located. The solids-lean supernatant may be decanted from the surface or proximate the surface of the liquid in the SBR vessel via an outlet valve or pump. The degree of sharpness of the supernatant/sludge interface may vary based on, for example, the type of wastewater and amount and type of suspended solids, ambient temperature or temperature within the SBR, and other factors. When the sludge and/or liquid level sensors identifies that the desired depth of supernatant having the desired low solids content has formed, the control system of the SBR initiates decanting of the solids-lean supernatant. The flow rate of decanted solids-lean supernatant is controlled to maintain the desired depth of supernatant with the desired low solids content throughout the decant process.

Figure 12:
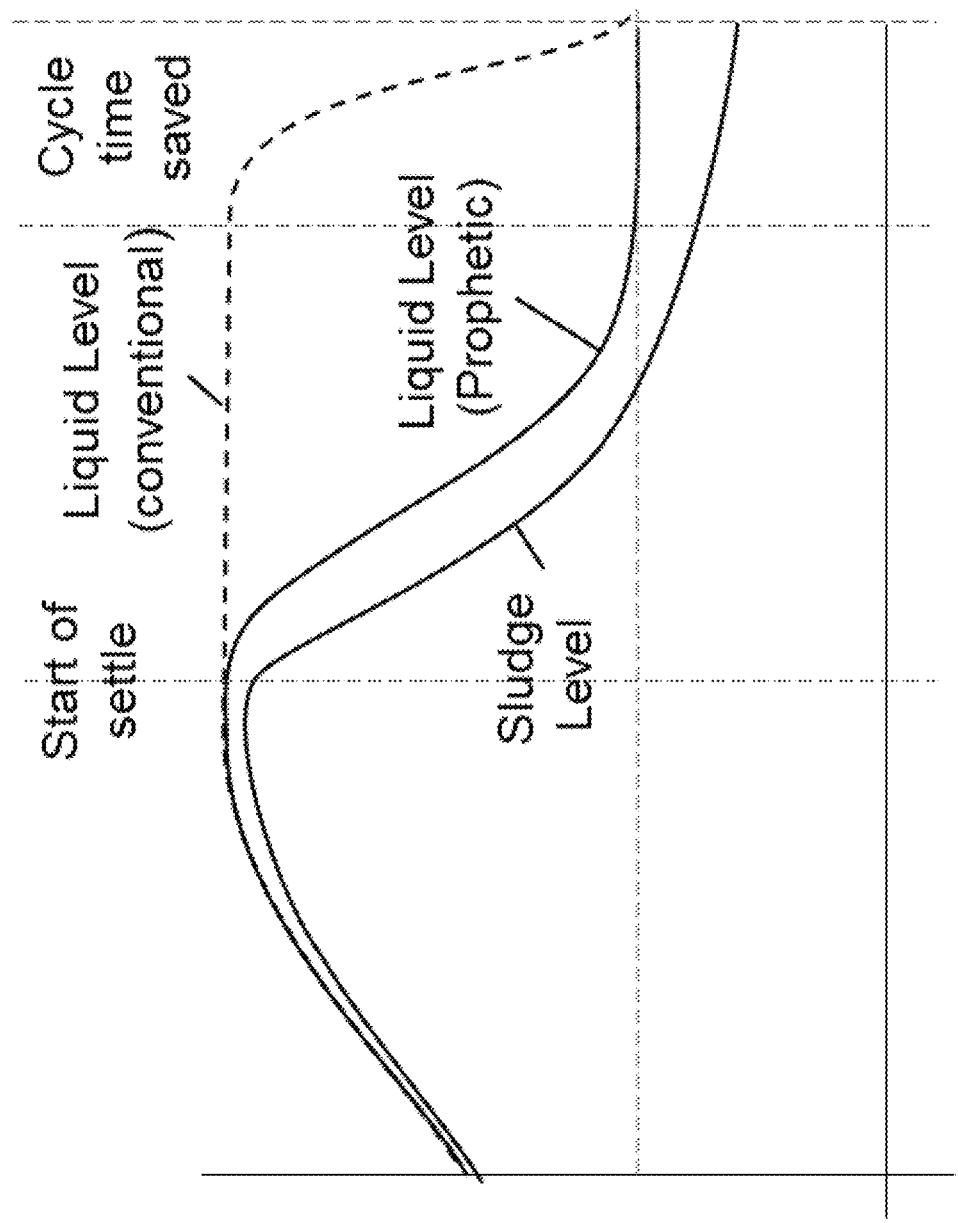
FIG. 12 prophetically illustrates sludge and liquid levels in an operating mode of an SBR as disclosed herein.

FIG. 12 represents liquid and sludge levels in one prophetic example of this process. In FIG. 12 the dashed line represents the overall liquid level in a conventionally operated SBR during an operating cycle. The SBR is filled, aerated, and the sludge is then allowed to settle. After settle time elapses the SBR decants the prescribed volume of solids-lean supernatant in preparation for the next cycle. The line labelled "Sludge Level" in FIG. 12 represents the depth of the sludge/supernatant interface. The solid line labelled "Liquid Level (Prophetic)" represents a potentially revised liquid level profile achievable while monitoring the sludge depth and decanting solids-lean supernatant to maintain a fixed supernatant depth in the SBR. By knowing where the sludge/supernatant interface is during the settle cycle some, or all, of the decant cycle may be performed concurrent with the settle cycle.

In one particular prophetic example, an SBR is normally operated with a 2.5 hour timed fill stage, a one hour timed react stage, a one hour timed settle stage, and a 25 minute timed decant/idle stage. The sludge settles to form solids-lean supernatant with sufficiently low solids content to meet regulatory guidelines for environmental discharge at a linear rate of about two inches/min (5.1 cm/minute). The time to achieve six inches of supernatant during the settling cycle would thus be about 3 minutes. If the system was modified to operate in accordance with one or more of the embodiments disclosed herein, the decant stage could then begin 3 minutes into the settle stage and the rate of solids-lean supernatant removal would be adjusted to maintain the six inches of supernatant with the sufficiently low solids content above the sludge/supernatant interface. The decant stage would end at substantially the same time as the settle stage.

The SBR cycle time would thus be reduced from four hours and 55 minutes to 4.5 hours, an 8.5% reduction. More wastewater flow may thus be treated in the same SBR footprint or the SBR footprint may be reduced by 8.5% and achieve the same wastewater treatment flow. For example, the number of SBR cycles could be increased from about 10 every two days to about 11 every two days, an increase of about 180 cycles per year. This reduction in cycle time would be greater for systems in which sludge settled faster, for example, in systems where magnetite was added to the sludge to enhance settling, and lesser in systems where sludge settling proceeded at a lower rate or where a greater depth of supernatant was desired to be maintained above the sludge/supernatant interface during decanting, for example, to meet stricter guidelines for solids content of solids-lean supernatant to be discharged to the environment.

Example 4: Prophetic Increase in Supernatant Recovery

The amount of solids-lean supernatant that is decanted during each cycle of an SBR is typically set at a fixed value. The fixed value is typically set so that during decanting the level of supernatant does not drop to a level close enough to the highest expected depth of the sludge/supernatant interface such that the decanted solids-lean supernatant does not include more suspended solids than allowed per local regulatory guidelines. Due to the variability in the depth of the sludge/supernatant interface below the surface of liquid in a typical SBR after a typical timed settle stage, the sludge/supernatant interface between the supernatant and settled sludge may be below the highest expected depth during many cycles. Decanting the fixed value of solids-lean supernatant in cycles in which the sludge/supernatant interface between the supernatant and settled sludge is below the highest expected depth may result in solids-lean supernatant that would meet regulatory guidelines for discharge remaining in the SBR after the decant stage, and the SBR may thus be operating below its optimal solids-lean supernatant production and wastewater treatment capacity and efficiency. By monitoring the depth of the sludge/supernatant interface, an amount of solids-lean supernatant that is decanted may be varied based on the observed depth of the sludge/supernatant interface, resulting in a greater amount of solids-lean supernatant that meets regulatory guidelines being decanted and increasing the solids-lean supernatant production and wastewater treatment capacity and efficiency of the SBR.

In one particular prophetic example, the sludge/supernatant interface depth after sludge settling in an SBR with an average liquid fill volume of 1,000 ft³ (28.3 m³) and average liquid fill height of 10 feet (with insignificant cycle-to-cycle fill height variation for this example) has a mean depth D of five feet (1.5 meters) with a standard deviation δ of one foot (0.3 meters). For solids-lean supernatant having a solids content meeting regulatory guidelines to be decanted with a confidence level of 99.9%, a set volume of solids-lean supernatant is decanted such that decanting stops when the supernatant level reaches one foot above D+3δ, or nine feet. If the level of the sludge/supernatant interface was monitored, on average, the solids-lean supernatant could be decanted until the supernatant level reached one foot above D, or six feet, while still meeting regulatory requirements for solids content. This would result in an average of an additional 300 ft$^3$ (8.5 m$^3$) of solids-lean supernatant being decanted for each cycle. If each cycle lasted an average of 6 hours, this would result in an increased solids-lean supernatant production capacity and wastewater treatment capacity of about 438,000 ft$^3$ (12,402 m$^3$) per year for the SBR.

The phraseology and terminology used herein is for the purpose of description and should not be regarded as limiting. As used herein, the term "plurality" refers to two or more items or components. The terms "comprising," "including," "carrying," "having," "containing," and "involving," whether in the written description or the claims and the like, are open-ended terms, i.e., to mean "including but not limited to." Thus, the use of such terms is meant to encompass the items listed thereafter, and equivalents thereof, as well as additional items. Only the transitional phrases "consisting of" and "consisting essentially of," are closed or semi-closed transitional phrases, respectively, with respect to the claims. Use of ordinal terms such as "first," "second," "third," and the like in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Having thus described several aspects of at least one embodiment, it is to be appreciated various alterations, modifications, and improvements will readily occur to those skilled in the art. For example, it should be appreciated that any of the level sensors and sludge sensors disclosed herein may be included in a wastewater treatment vessel or SBR with any other of the level sensors and sludge sensors disclosed herein. Any feature described in any embodiment may be included in or substituted for any feature of any other embodiment. In further embodiments, existing wastewater treatment systems or vessels may be retrofitted to include features of the wastewater vessels disclosed herein. Such alterations, modifications, and improvements are intended to be part of this disclosure, and are intended to be within the scope of the invention. Accordingly, the foregoing description and drawings are by way of example only.

What is claimed is:

1. A wastewater treatment system comprising:
a sequencing batch reactor vessel configured to perform biological treatment of wastewater in a series of treatment stages including a fill stage, a biological reaction stage, a sludge settling stage in which solids settle from the wastewater to form a sludge and a solids-lean supernatant, a solids-lean supernatant decant stage, and an idle stage, the fill stage including introducing a non-predetermined amount of wastewater into the vessel;
a liquid level sensor configured to measure a level of liquid in the vessel and provide an indication of the level of the liquid to a controller; and
a sludge detector configured to measure a position of an interface between the sludge and the solids-lean supernatant in the vessel and to provide an indication of the position of the interface to the controller, the controller configured to perform a comparison between the level of the liquid and the position of the interface and control an amount of solids-lean supernatant removed from the vessel during the decant stage based on the comparison.

2. The system of claim 1, wherein the sludge detector is further configured to determine a degree of sharpness of the interface and to provide an indication of the degree of sharpness of the interface to the controller.

3. The system of claim 2, wherein the controller is further configured to initiate removal of the solids-lean supernatant responsive to the degree of sharpness of the interface exceeding a predetermined level.

4. The system of claim 2, wherein the controller is further configured to vary a speed of removal of the solids-lean supernatant based at least in part on the degree of sharpness of the interface.

5. The system of claim 2, wherein the controller is further configured to control a rate of sludge removal from the vessel based at least in part on the degree of sharpness of the interface.

6. The system of claim 1, wherein the controller is further configured to decant solids-lean supernatant vessel at a rate that maintains a substantially constant depth of supernatant above the interface.

7. The system of claim 1, wherein the controller is further configured to control an amount of sludge removed from the vessel based at least in part on the position of the interface.

8. The system of claim 1, wherein the sludge detector comprises a plurality of suspended solids sensors each disposed at different fixed locations within the vessel.

9. The system of claim 8, wherein the plurality of suspended solids sensors comprise one or more of optical sensors or ultrasonic sensors.

10. The system of claim 1, wherein the sludge detector comprises a sensor that moves vertically responsive to a change in the level of liquid in the vessel.

11. The system of claim 10, wherein the sludge detector comprises one of an ultrasonic level sensor or a radar level sensor.

12. The system of claim 1, wherein the liquid level sensor comprises an ultrasonic sensor.

13. The system of claim 1, wherein the liquid level sensor comprises a plurality of sensors each disposed at different fixed levels in the vessel.

14. The system of claim 1, wherein the sludge detector comprises an ultrasonic level detector having an operating frequency between about 50 kHz and about 800 kHz.

15. The system of claim 1, wherein the sludge detector comprises a compressed high-intensity radar pulse sonar unit.

* * * * *